United States Patent [19]
Slomski

[11] 3,973,332
[45] Aug. 10, 1976

[54] EQUIPMENT FOR TESTING THE KINESTHETIC ABILITIES OF A PERSON'S EXTREMITIES

[76] Inventor: Waclaw Kazimierz Slomski, 426 Wilkinson St., Syracuse, N.Y. 13204

[22] Filed: Jan. 28, 1975

[21] Appl. No.: 544,202

[52] U.S. Cl. .............................. 35/22 R; 73/132; 73/379; 273/DIG. 5
[51] Int. Cl.² ................. G09B 19/00; G01L 5/22
[58] Field of Search ............ 35/11 R, 22 R; 73/132, 73/379; 272/DIG. 5

[56] References Cited
UNITED STATES PATENTS

| | | | |
|---|---|---|---|
| 1,684,639 | 9/1928 | Sanford | 73/132 |
| 2,177,501 | 10/1939 | Smalley | 35/11 R |
| 2,659,164 | 11/1953 | Durham | 35/11 R |
| 2,979,831 | 4/1961 | Bullock | 35/11 R |
| 3,613,440 | 10/1971 | Tinkham | 73/132 |
| 3,641,686 | 2/1972 | Krass | 35/22 R |

FOREIGN PATENTS OR APPLICATIONS
134,822   2/1920   United Kingdom ................. 35/22 R

*Primary Examiner*—William H. Grieb
*Attorney, Agent, or Firm*—Mason, Mason & Albright

[57] ABSTRACT

The equipment tests kinesthesic abilities of the tested person's extremities. Although it tests psychologically drivers of all kinds of motor vehicles, this equipment can be also used in a variety of different situations.

The equipment consists of the following elements: (a) controlling and recording module; (b) dynamometer with a pressure indicator, which is connected with the recording module; (c) an adjustable seat for the tested person. In the testing method the dynamometer pedal is pressed with a certain strength. The tested person must remember this strain and repeat the procedure several times. The preliminary pressure and the subsequent ones are registered on the recording module in numerical form.

5 Claims, 8 Drawing Figures

EQUIPMENT FOR TESTING THE KINESTHETIC ABILITIES OF A PERSON'S EXTREMITIES

BACKGROUND OF THE INVENTION

The enormous development of street and highway traffic results in a steadily growing number of traffic accidents. These accidents bring about great material losses and, more importantly are incommensurable in relation to human losses: loss of life, or permanent invalidism. The safety of traffic on the highways and streets depends to a considerable degree on the fact that a driver will in a definite traffic situation react in a proper way and sufficiently fast. The psychology of street and highway traffic attempts to define these problems. The subject of its investigation is a detailed analysis of the driver's work, in order to establish pscho-physiological functions, indispensable for its safe execution. The driver's work has a specific character. In addition to some acquired information, training and possession of driving competence, the driver is also required to possess a particular psycho-physiological competence, considering the dynamics of the driven vehicle, and the human life and health hazards connected with it.

Among the great number of drivers, travelling on the streets and highways, there are some, who often do not realize that they have certain psycho-physiological deficiencies. This is why a necessity arises for controlliing psycho-physiological characteristics of drivers before their licensing and during their execution of work, as concerns changes or disappearance of psycho-physiological competence.

The proper evaluation of psycho-physiological characteristics of a driver can be made only by using certain arrangements, specialized and adapted for this aim. One of these arrangements, which serve such aims, is my present invention. It can be used for studying the precision of motions connected with the tremor of hands which appears with illnesses of the nervous system, alcoholism, and old age. This device has been already successfully tested in several cases for determining the presence and degree of such afflictions.

With the help of this equipment, one can study the sensitivity of the sense of kinesthesia.

The testing of this psycho-physiological function is very important because the use of the gas, clutch and brake pedals in all sorts of motor vehicles requires an adequate kinesthetic sensitivity and a competence for remembering and properly reproducing the leg pressure strain.

DETAILED DESCRIPTION

The invention comprises the feature of construction, combination of elements, and arrangement of parts, which will be exemplified in the construction hereinafter set forth, and the scope of the invention will be indicated in the claims.

This invention is intended for testing psychologically drivers of all kinds of motor vehicles. The device is used for testing the uniformity of leg pressure on an appropriate pedal of a mechanism from the point of view of the so-called "Kinesthetic memory." This kind of test is very important for people who in their work operate on pedals, such as gas, clutch, and brake, and also on other types of levers, and where an appropriate kinesthetic sensitivity is required, i.e., the competence of remembering and properly reproducing the same leg pressure. The instrument is one of a set of devices for psycho-physiological testing of drivers of various types of motor vehicles. The set of these devices creates a method of testing, the aim of which is the reduction of traffic accidents.

For a fuller understanding of the nature and objects of the invention, reference should be had to the following detailed description taken in connection with the accompanying drawings, in which.

The apparatus comprises a whole testing system. On the metal base, in its front part, is a structure encased in a metal cover where, in the upper part of this structure, all elements and also control-and-recording units are located. On the inside part of the casing, on the inclined wall, a dynamometer is located together with the measuring system. In the back of the equipment, a seat for the tested person is located. This seat is equipped with guide-bars, which make possible its adjustment forward or to the back.

Figure 1:
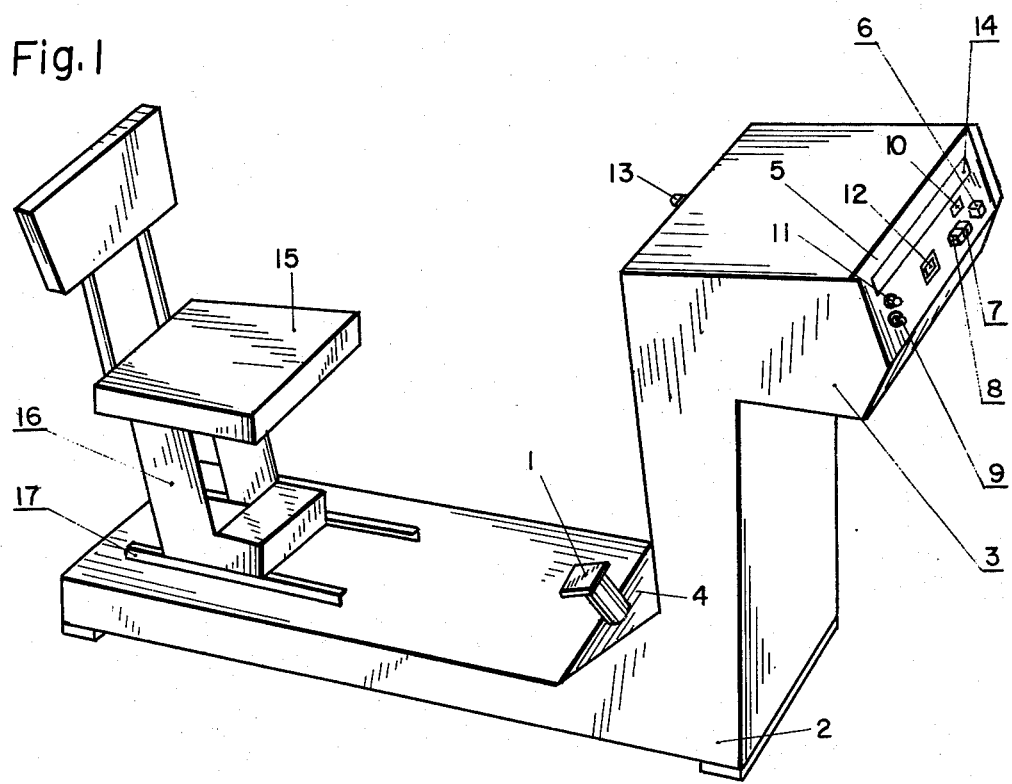
FIG. 1 represents the general perspective view of the equipment.

FIG. 1 shows the general perspective view of the equipment. In the casing 3 of the equipment, on its inclined wall 5, are located the following elements: the recording scale 14, the key-type switches in a common enclosure, the key-type switch 8 for connecting the supply 115-V network current, the key-type switch 7 for connecting the supply of 24-V equipment current, and the trip button 6, which serves to erase the test results. The turning on of the supply 115-V current is indicated by a signal lamp 10. The control lamp 12 signals the testing person that the equipment is ready for testing. The control lamp 13 signals the tested person that testing has started.

On the inclined wall 4, which is close to the base 2 of the equipment, a measuring dynamometric system 1 is located. The seat 15 has a base 16, which in its lower part can shift in guide bars 17, which permits for longitudinal adjustments of the seat 15.

Figure 2:
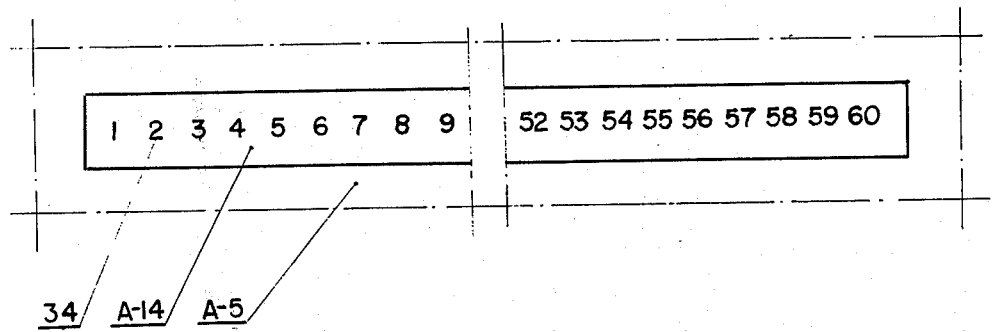
FIG. 2 represents the recording scale of the system, recording the results of measurements.

FIG. 2 shows the recording scale A-14, which registers the results of the tests. The scale is made from plexiglass. On its inner side the scale is painted in black with digits engraved on it; these digits fall in line with corresponding measuring degrees of the dynamometrical system. As example, the digit 2, which is designated on FIG. 2 as 34. The measuring scale A-14 is located on the inclined wall A-5 of the equipment casing.

Figure 3:
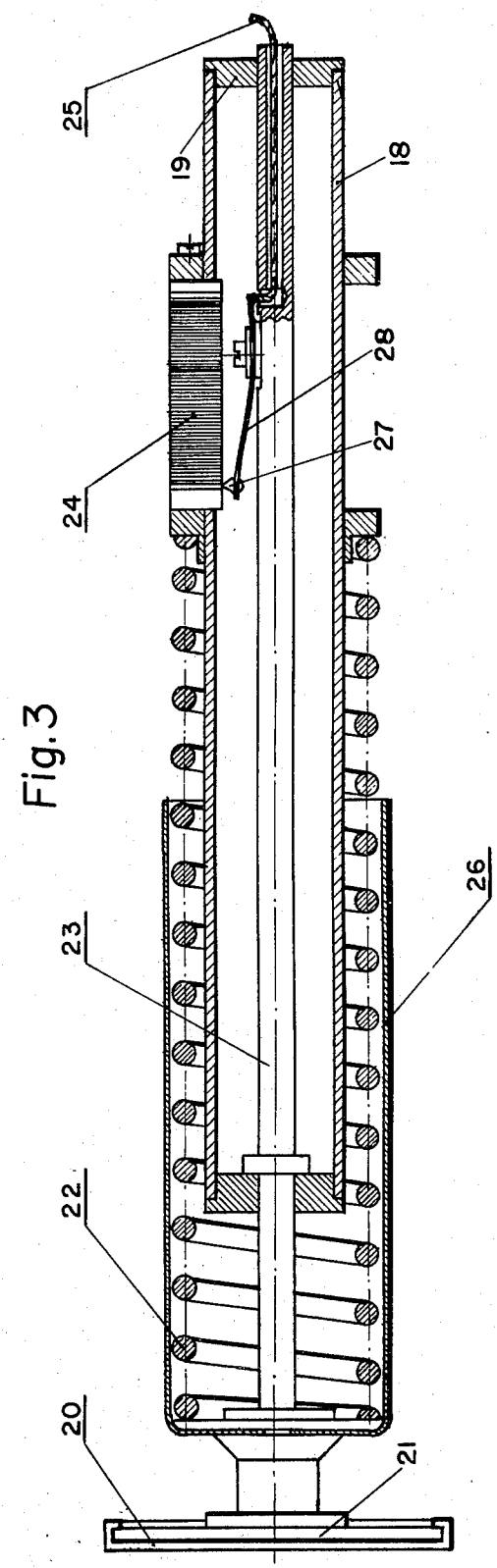
FIG. 3 represents the cross-section of the dynamometric unit, which is connected with the recording unit of the equipment.

FIG. 3 shows in a cross-section the dynamometric system, which is connected with the measuring system of the equipment. The dynamometric system, together with the measuring system, are connected in one whole unit, which is fixed on the inclined wall 4 of FIG. 1. The upper part of the dynamometric system sticks out from the inclined wall 4 and one can see only the pedal 21, with the rubber cover-plate 20, and the metal cover 26.

The dynamometric system comprises the following parts: pedal 21, rubber cover-plate 20 of the pedal, spring 22, metal cover 26 of the spring, rod 23, guide member 19 of the rod, and casing 18. On the casing 18 the measuring system 24 is mounted.

The measuring system comprises a series of special thin metal measuring plates, which are separated from each other by insulating sheets. From every measuring plate a conductor leads, which connects a corresponding relay.

After pressing the pedal 21, rod 23 shifts in guide member 19; rod 23 pulls the brush 28, which slides with its contact 27 on measuring elements where a connection occurs between the corresponding measuring elements and the contact 27 of the brush 28. The conductor 25 leads from the brush 28 to corresponding relays.

Every pushing down of the pedal 21 with a certain strength causes a shift of rod 23, and, simultaneously, a shift of brush 28 and contact 27 which are connected with the rod 23; the brush shifts for constant distances. The spring characteristics are selected in such a way that the pushing down of the pedal 21 with the strength of one pound causes the shift of the contact 27 by one measuring element. For example, the pushing down of the pedal 21 with the strength of 10 lbs, causes the shift of the brush contact 27 to the tenth measuring element.

Figure 4:
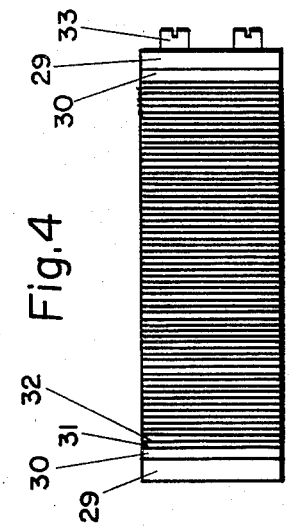
FIG. 4 represents a side view of the measuring element of the equipment.

FIG. 4 represents a side elevation of the measuring system. The separate elements of this system are fastened with screws, of which one only is designated as 33. The end plates 29 are made from an insulating material, and serve for fastening the measuring system in the casing 18, FIG. 3. Contact plates 30, measuring elements 31, and insulating sheet 32, separating the measuring elements, are the elements of the measuring system.

Figure 5:
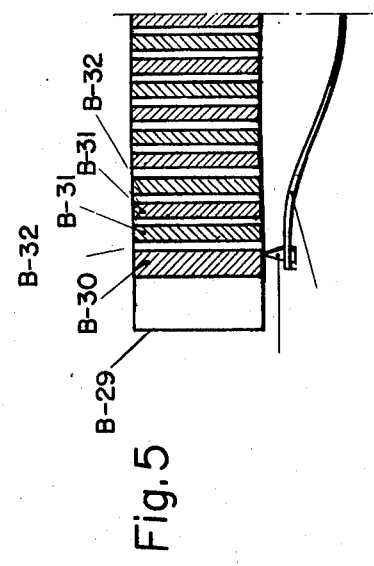
FIG. 5 represents the cross-section of a fragment of the measuring element of the equipment.

FIG. 5 presents in cross-section a first fragment of the measuring system.

The insulating sheet B-29 at the end separates the contact plate B-30. On the B-30 contact plate the contact B-27 of the brush B-28 is placed. This is the initial position before the beginning of the tests. The placing of the contact B-27 on the contact plate B-30 serves for switching-on the control lamps 12 and 13, which indicates the readiness of the equipment for carrying on the test. As the pedal 21, FIG. 3, is being pressed, the brush B-28 shifts with its contact B-27 along the measuring elements B-31 to sheet B-32 then to a further adjacent element B-31 and so forth, all the way to the end element B-30. This fact of pushing the brush B-28 with its contact B-27 to the extreme position of the end plate B-30, FIG. 4, is signaled by a buzzer.

METHOD OF CONDUCTING THE TEST

The tested person sits comfortably on the seat 15, FIG. 1, leaning against the back. As necessary, the tested person adjusts the seat in order to be able to easily press with the leg the dynamometric measuring system 1, FIG. 1.

The testing person switches-in the equipment by pressing in turn the switch 8 and the switch 7, FIG. 1. The switching-in of the equipment to the 115-V current network is signaled by the signal lamp 10, FIG. 1. After the pressing of switches 8 and 7, FIG. 1, the equipment is ready for testing. The tested person is informed about it by the control lamp 13, FIG. 1, and the testing person by the control lamp 12, FIG. 1.

The test comprises the repeated pressing with the leg by the tested person on the pedal of the dynamometric measuring system, using for this purpose a certain effort. The tested person has to remember what effort was used for this pressing, then release the pedal, and repeat a couple of times the pressure, trying to accomplish the same rate of pressure as initially.

The testing is repeated again, with pressing the pedal using a strong effort, medium effort, and weak effort, every time trying to repeat the given initial pressure. The pressing of the pedal to the bottom, i.e., to the stop, is signaled by an acoustic signal. Results of the measurement are recorded on the recording scale A-14, FIG. 2. Every digit on the recording scale, lighted from below, indicates the corresponding force in lbs. applied on the pedal of the dynamometric system. Every pressing on the pedal by the tested person is recorded on the recording scale 14, FIG. 1, and automatically locked there until the end of the testing period. After writing down the results of the test, the testing person presses the button 6, FIG. 1, and in this way cancels the record from the measuring scale. After this cancelling, the control lamps 12 and 13, FIG. 1, become lighted, thus indicating that the equipment is ready for the next test. The greatest deviations from the initial pressure in all three types of pressure-light, medium and strong, are taken as the results of the test for qualifying the tested person.

Figure 6A:
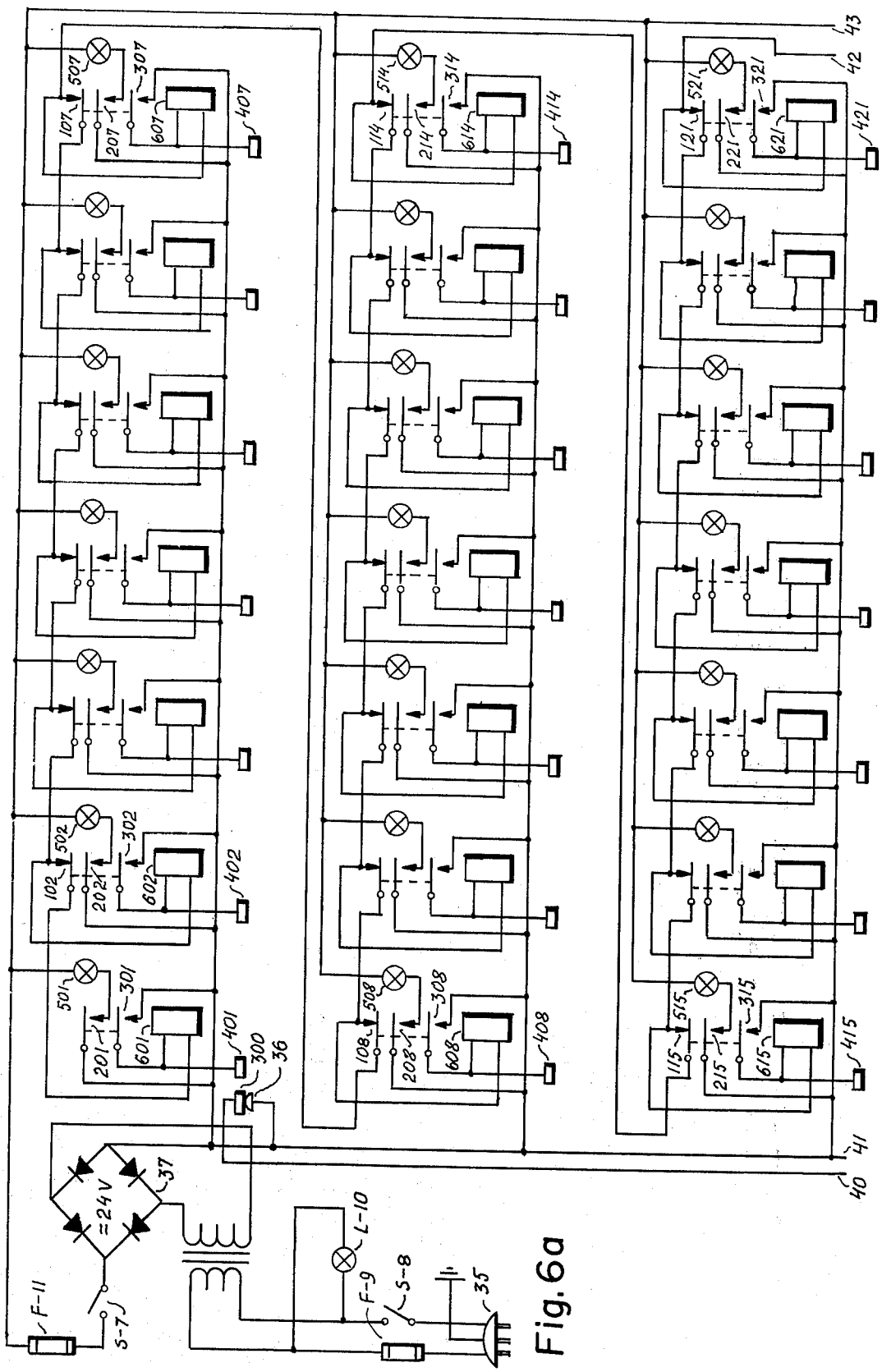
FIG. 6a represents the electric connections diagram of the equipment — part 1.
Figure 6B:
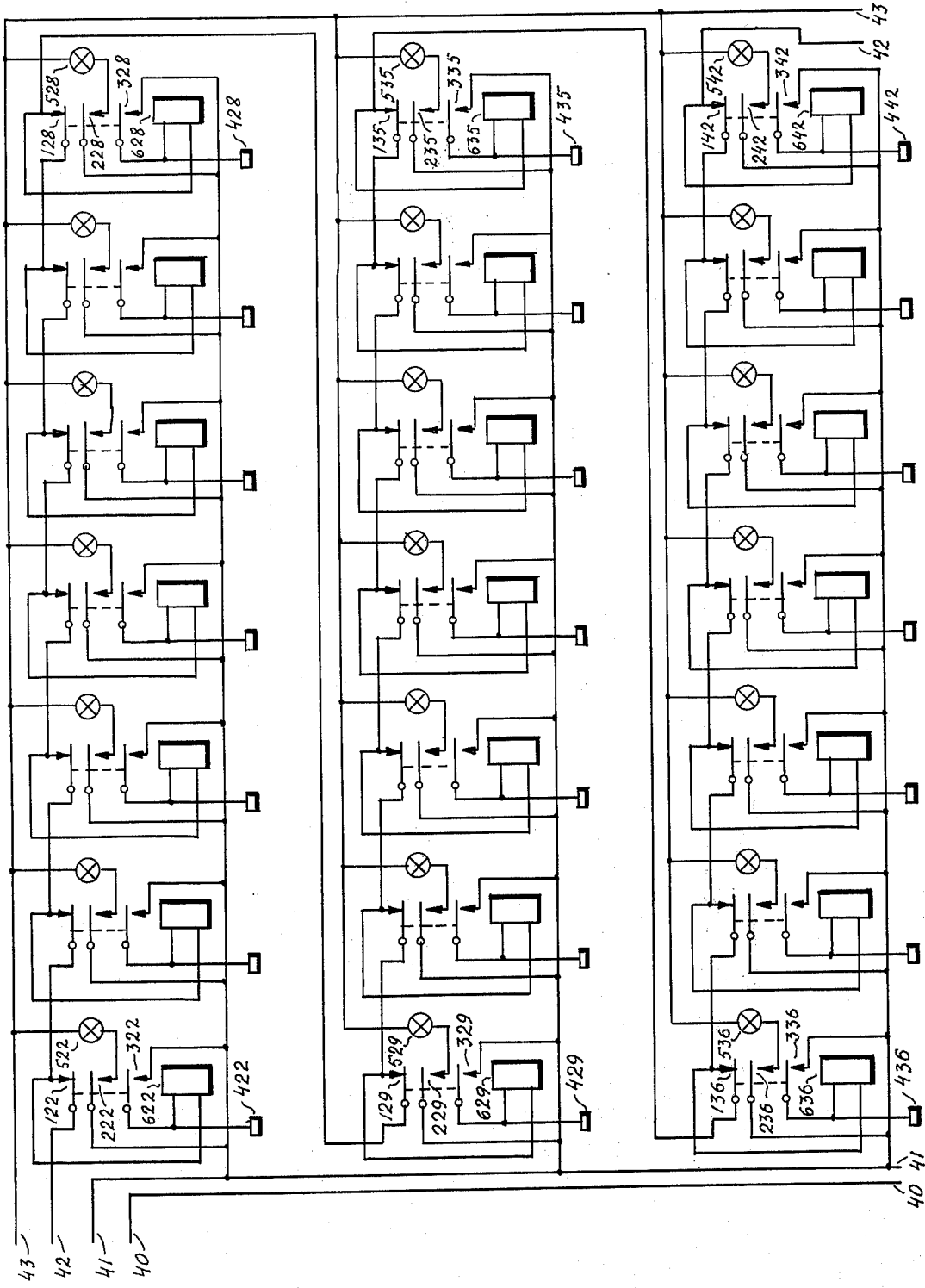
FIG. 6b represents the electric connections diagram of the equipment — part 2.

FIG. 6a represents the electric connections diagram of the equipment. This diagram is presented on three FIGS: 6a, 6b and 6c. The relays constitute the main electric elements of the equipment. Every relay, except the first one, have two pairs of break contacts and one pair of operating contacts. The equipment comprises 60 relays, to each of which corresponds a measuring element. On FIG. 6a, FIG. 6b, and FIG. 6c, the relays are designated with numbers from 601 to 660. The separate measuring elements of these relays are designated with numbers from 401 to 460. The lamps providing illumination from below the digits of the measuring system, corresponding to the separate measuring elements, are designated on the electric connections diagrams with numbers from 501 to 560.

The equipment is supplied from the 115-V/60Hz electric network through a transformer and rectifier 37 which supplies a 24-V electric current to the various elements of the equipment.

After the connection of the plug 35 to the socket of the 115-V/60Hz network, and switching in the switch S-8, the signal lamp L-10 lights, and the rectifier 37 is connected to the 24-V electric network of the equipment. The fuse F-9 serves for protecting the 115-V network, and the fuse F-11 protects the 24-V network. After switching-in the switch S-7, the equipment is ready for starting the test. At this moment, the contact 36, FIG. 6a, of the brush B-28, FIG. 5, is placed on the end plate 300, FIG. 6a. The current flows through the conductor 40 to the relay 50, FIG. 6c. After the pressing of the button S-6 (FIG. 6c), the relay 50 is switched-in, and it switches the control lamps L-12 and L-13 through the contacts 52, FIG. 6c. The lighting of the control lamps L-12 and L-13 gives the sign to start the testing. The contacts 51, FIG. 6c, serve for locking the relay 50, FIG. 6c. After the tested person presses on the pedal of the dynamometric system, the contact 36, FIG. 6a, shifts on the separate measuring elements.

Figure 6C:
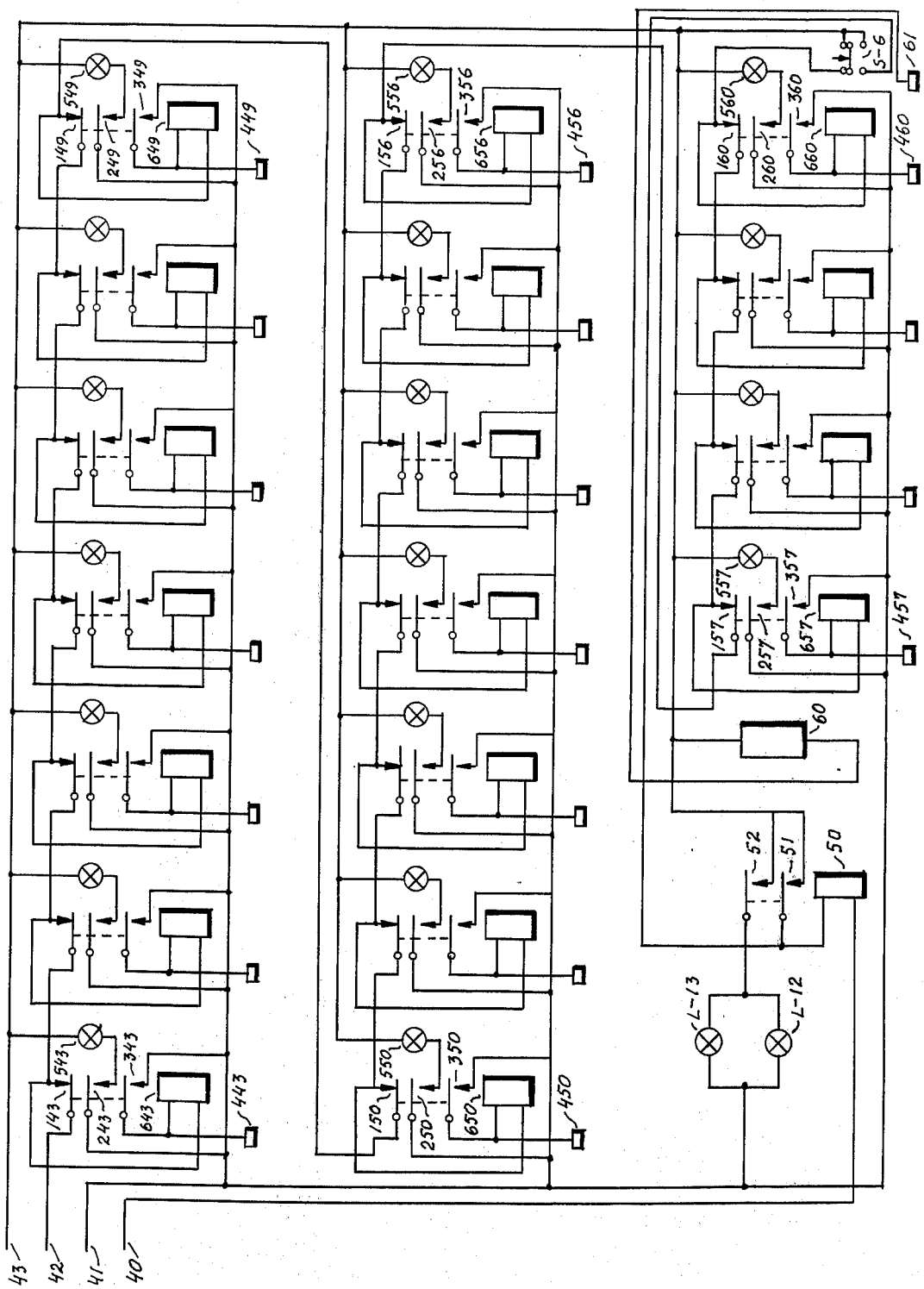
FIG. 6c represents the electric connections diagram of the equipment — part 3.

After the contact 36 leaves the end plate 300, FIG. 6a, the flow of the current to the relay 50, FIG. 6c, is interrupted, and both signal lamps L-12 and L-13 are switched off. For example, if the tested person will press the pedal of the dynamometric system with a strength of 14 lbs., then the contact 36, FIG. 6a, will shortcircuit the measuring element 414, and the relay 614 will be activated. The activation of the relay 614 will cause: shortcircuiting of the contacts 314, which are locking the relay; short-circuiting the contacts 214, which will light the lamp 514, thus lighting from below the digit 14 on the recording scale, FIG. 2, and the contacts 114 will be opened, thus cutting off the supply of current to the relay 613, and will switch it off. The activation of the relay 615 will cause the opening of the contacts 115 and the switching off the relay 614. The given relay remains locked as long as there is no shifting of the contact 36, FIG. 6a, to the next measuring element.

The shifting of the contact 36 to the last contact plate of the measuring system will activate the buzzer 60, FIG. 6c. After the writing down of the results of the test, the testing person presses the button S-6, FIG. 6c, which turns off the current supply to the given relay, which was switched on at the given moment and this relay is cut off. Meanwhile, the pressing of the button S-6 by the testing person, switches on the relay 50, which will cause the lighting of the control lamps L-12 and L-13, indicating that the equipment is ready for the next test.

By analyzing the results obtained during the tests one will be able to evaluate the tested person as to the degree of the given psycho-physiological features possessed and thereby to foresee good or bad results in performing the tasks for which the person was tested.

The above described equipment has been built in a model. All its electric and mechanical systems operate accurately, and meet perfectly the requirements. The equipment can unreservedly be used for psychological tests.

Having described my invention, what I claim as new, and desire to secure by Letters Patent, is:

1. Apparatus for testing kinesthetic memory which comprises:
   a rod including means for receiving a force exerted by the person being tested, said rod being moved by said force;
   resilient means connected to said rod opposing with a progressively increasing counterforce the movement of said rod caused by said exerted force;
   indicator means responsive to movement of said rod caused by said exerted force, said indicator means comprising circuit means, movement discrimination means responsive to the relative movement of said rod included in said circuit means, and indicia means interconnected into said circuit means whereby the amount of force applied to said rod in an individual test is registered by said indicia means, said indicia means comprising a series of separate characters for individually indicating the various forces which may be applied to said rod, said circuit means including clamping means for maintaining differentially relative to the other said characters in registration in said indicia means only one character of said series of characters, said one character indicating the highest force attained in each individual test; and
   reset means for inactivating said clamping means for further individual tests.

2. Apparatus for testing kinesthetic memory in accordance with claim 1, wherein amounts of movement of said rod are proportional to said forces applied thereto.

3. Apparatus for testing kinesthetic memory in accordance with claim 1, wherein said rod is displaced in a direction of its longitudinal axis when moved by the application of force thereto, said resilient means comprising a compression spring which at least in part surrounds said rod.

4. Apparatus for testing kinesthetic memory in accordance with claim 1, wherein said indicator means comprises an electrical circuit, a contact from said electrical circuit connected to said rod, a plurality of segments rigidly secured relative to the apparatus adapted to receive said contact one-by-one in accordance with movement by said rod relative to said plurality of segments, said circuit connecting said segments separately to said indicia means whereby the amount of force applied to said rod is registered by said indicia means.

5. Apparatus for testing kinesthetic memory in accordance with claim 4, wherein said indicia means comprises a series of numbers indicating in unit measures for force.

* * * * *